United States Patent [19]
Hobeika

[11] Patent Number: 6,027,532
[45] Date of Patent: Feb. 22, 2000

[54] EAR VENT DEVICE AND METHOD OF INSERTING THE SAME

[76] Inventor: Claude P. Hobeika, 10144 Spiritknoll La., Cincinnati, Ohio 45252

[21] Appl. No.: 09/006,605

[22] Filed: Jan. 13, 1998

[51] Int. Cl.⁷ .............................. A61F 2/18; A61F 11/00
[52] U.S. Cl. .............................................. 623/10; 606/109
[58] Field of Search ................................ 623/10; 606/109

[56] References Cited

U.S. PATENT DOCUMENTS

| | | |
|---|---|---|
| 3,948,271 | 4/1976 | Akiyama . |
| 4,094,303 | 6/1978 | Johnston . |
| 4,174,716 | 11/1979 | Treace . |
| 4,175,563 | 11/1979 | Arenberg et al. . |
| 4,675,008 | 6/1987 | Tretbar . |
| 4,744,792 | 5/1988 | Sander et al. . |
| 5,047,053 | 9/1991 | Jahn . |
| 5,433,748 | 7/1995 | Wellisz ........................................ 623/10 |
| 5,645,584 | 7/1997 | Suyama . |

FOREIGN PATENT DOCUMENTS

| | | | |
|---|---|---|---|
| 1326276 | 7/1987 | U.S.S.R. | ................................ 606/109 |
| 1500316 | 8/1989 | U.S.S.R. | ................................ 606/109 |

*Primary Examiner*—David H. Willse
*Attorney, Agent, or Firm*—Dinsmore & Shohl LLP

[57] ABSTRACT

An ear vent device for maintaining an aperture in ear tissue in an operable open condition, comprising a first panel having a first edge; and a second panel resiliently joined to the first panel along an apex in a substantially open, angular arrangement. A flange can be attached adjacent the first edge. In addition, the second panel can also comprise a first edge and have a flange adjacent the first edge of the second panel.

20 Claims, 4 Drawing Sheets

EAR VENT DEVICE AND METHOD OF INSERTING THE SAME

TECHNICAL FIELD OF THE INVENTION

The present invention relates generally to ear tube devices used in surgical procedures and methods for inserting the same into the eardrum, and more particularly, to devices that are inserted through and secured to the eardrum, and a method for inserting and securing the device to the eardrum.

BACKGROUND OF THE INVENTION

Often, because of ear infections and other ear problems, hearing can become impaired. It is common practice in the treatment of retracted tympanic membranes, serious otitis media, Eustachian tube malfunction and other middle ear problems to provide a small passageway in the tympanic membrane, which is commonly referred to as the eardrum. The passageway provides fluid communication between the middle ear cavity and outer ear cavity such that negative pressure can be relieved (i.e., to equalize pressure), so that excess fluid can be drained, and so that medicine can be injected into the middle ear cavity.

In the past, ear, or tympanotomy, tubes have been inserted into the passageway so that it does not heal (e.g., close) too quickly. Tubes generally have included enclosed lumens that provide fluid (e.g., gaseous and liquid) communication between the middle and outer ear cavities. More recently, there has been a demand for ear vent devices that provide a better anatomical fit within the tympanic membrane, are easier to insert and remove, and cause less trauma to the eardrum during insertion, during removal, and while in place.

Some prior implants, such as illustrated in U.S. Pat. No. 4,744,792 (Sander, et al.), are configured to have a generally elongated cylindrical shape with an enclosed lumen therein. Flanges typically being disc shaped are provided at the oppositely disposed ends of the tube such that the device resembles a spool or bobbin. The flanges assist to hold the tube in place in the surgically formed passageway in the tympanic membrane.

Other prior implant devices, such as illustrated in U.S. Pat. No. 4,675,085 (Tretbar), are generally T-shaped and are commonly referred to as T-tubes. The T-tube comprises a crossbar which can assist to hold the tube in place in the surgically formed passageway in the tympanic membrane. Moreover, the crossbar can assist to direct fluid(s) to the tube having an enclosed or internal lumen. The tube is passed through the membrane.

In many instances, however, when the incision is made longer or has to be L-shaped so that the tube and its flanges can be inserted into the tympanic membrane, the process for making the incision can further traumatize the eardrum. When the trauma will be too much for the patient to handle under a local anesthetic, the procedure to insert the tube will likely need to be performed in an operating room at the hospital with the patient being anesthetized with a general anesthetic. Such a procedure with a general anesthetic at the hospital is more costly and takes additional time for the patient due to increased preparation time for and recovery time from the general anesthetic and the additional trauma to the eardrum.

The incision made in the tympanic membrane, with fibers extending inwardly in a spoke-like fashion, provides a generally triangular shaped passageway or slit to receive the tube. Tubes for insertion into the tympanic membrane typically have a circular cross section (e.g., bobbin shaped tube) and/or an oversized flange (e.g., T-shaped tube), and thus traumatize the eardrum due to the dramatic geometric misfit between the tube and the opening. Moreover, the likelihood of extrusion of the tube from the tympanic membrane is further increased as well due to the geometric misfit. This geometric misfit is believed to result in scaring of the tympanic membrane once the tube is removed. Moreover, tubes with non-collapsible flanges will further traumatize the eardrum as the tube is removed or otherwise extruded from the eardrum.

Currently available tubes with a circular cross section have flanges at the end that extend around the entire periphery of the tube opening so as to provide a disc shaped flange to anchor and stabilize the ear tube in the tympanic membrane so that the tube is supported and secured therein, and so that the tube is not easily extruded. In many instances, however, the flanges, especially when wide or oversized, can traumatize the tympanic membrane over time. This trauma to the tympanic membrane can limit the time period in which the ear tube can remain in the tympanic membrane. Consequently, in some instances, the ear tube has to be removed to limit additional trauma to the eardrum. This can result in the need to repeat the procedure for providing a passageway between the middle and outer ear cavities and inserting a tube therein.

As can be seen, currently available implants have a number of shortcomings that can greatly reduce the ability of the implant to remain in the tympanic membrane and perform their intended function. The current structures and assemblies provide an implant that can damage or traumatize the recipient site area in the tympanic membrane, which in turn, can hamper or interfere with an implant's ability to assist in healing the eardrum. In addition, the trauma inflicted by the implant can weaken the eardrum and can contribute to further complications. Moreover, some implants are not easily inserted into the slit or passageway in the tympanic membrane. A need currently exists in the ear tube industry for an implant that is more easily inserted into or through the tympanic membrane, and is configured to minimize further trauma to the ear and the tympanic membrane.

SUMMARY OF THE INVENTION

It is an object of the present invention to provide an ear vent device that addresses and overcomes the above-mentioned problems and shortcomings in the ear implant industry.

It is a further object of the present invention to provide an improved ear vent device that reduces the possibility of extrusion of the tube into the outer ear cavity.

It is also an object of the present invention to provide an improved ear vent device that reduces the need for an oversized incision in the tympanic membrane.

It is yet another object of the present invention to provide an improved ear vent device for maintaining a passageway in the tympanic membrane.

It is another object of the present invention to provide an improved ear vent device that secures the device to the tympanic membrane.

It is further an object of the present invention to provide an improved ear vent device that is sizable to fit a particular anatomical situation.

It is still another object of the present invention to provide an improved ear vent tube that provides a reliable channel for fluid discharge.

It is yet an object of the present invention to provide an improved ear vent tube that is easier and faster to install in patients with less discomfort.

Yet another object of the present invention is to provide an improved ear vent tube that decreases healing time after the ear vent tube is inserted.

Still a further object of the present invention is to provide an improved ear vent tube that can be installed and/or removed more quickly with less trauma to the eardrum.

Another object of the present invention is to provide an improved ear vent device that provides a sufficient channel for the safe passage of devices and/or medication through the tympanic membrane.

A further object of the present invention is to provide an improved ear vent tube that enhances preservation of tissue surrounding the ear vent tube.

Additional objects, advantages and other features of the invention will be set forth and will become apparent to those skilled in the art upon examination of the following, or may be learned with practice of the invention.

To achieve the foregoing and other objects, and in accordance with purpose herein, the present invention comprises an ear vent device for maintaining a passageway or aperture in the eardrum in an operable open condition, comprising a first panel having a first edge; and a second panel resiliently joined to the first panel along an apex in a substantially open, angular arrangement. A flange can be attached adjacent the first edge of the first panel. In addition, the second panel can also comprise a first edge and have a flange adjacent its first edge. The flanges of both panels are preferably non-contiguous with each other. In a preferred embodiment, each panel can comprise a second edge oppositely disposed from the first edge, and a flange adjacent each of the second edges.

The first wall and the second wall are preferably angularly oriented to each other at an angle from about 10 degrees to about 35 degrees, and more preferably about 17 degrees.

The flanges are provided to assist in preventing the device from being extruded from the tympanic membrane, and are preferably oriented relative to their respective panels at an angle of about 90 degrees. In addition, a portion of the panels adjacent the flanges can be cut to increase the surface area of the flanges to assist in preventing extrusion of the device.

While the device can be made from a number of known biocompatible materials, it is preferably made of a rubberized material and can be coated with a coating to either assist or retard tissue integration with the device, as desired.

In use, an incision is made in the eardrum to provide a passageway and the device is inserted into the passageway. After insertion, the device unfolds to an open operable/functional condition. To remove the device from the ear, the device is collapsed to its closed position, preferably by closing the panels together, and folding the flanges to be substantially parallel to the panels, and then withdrawn

BRIEF DESCRIPTION OF THE DRAWINGS

While the specification concludes with claims particularly pointing and distinctly claiming the present invention, it is believed the same will be better understood from the following description taken in conjunction with the accompanying drawings in which:

DETAILED DESCRIPTION OF THE PREFERRED EMBODIMENTS

Figure 1:
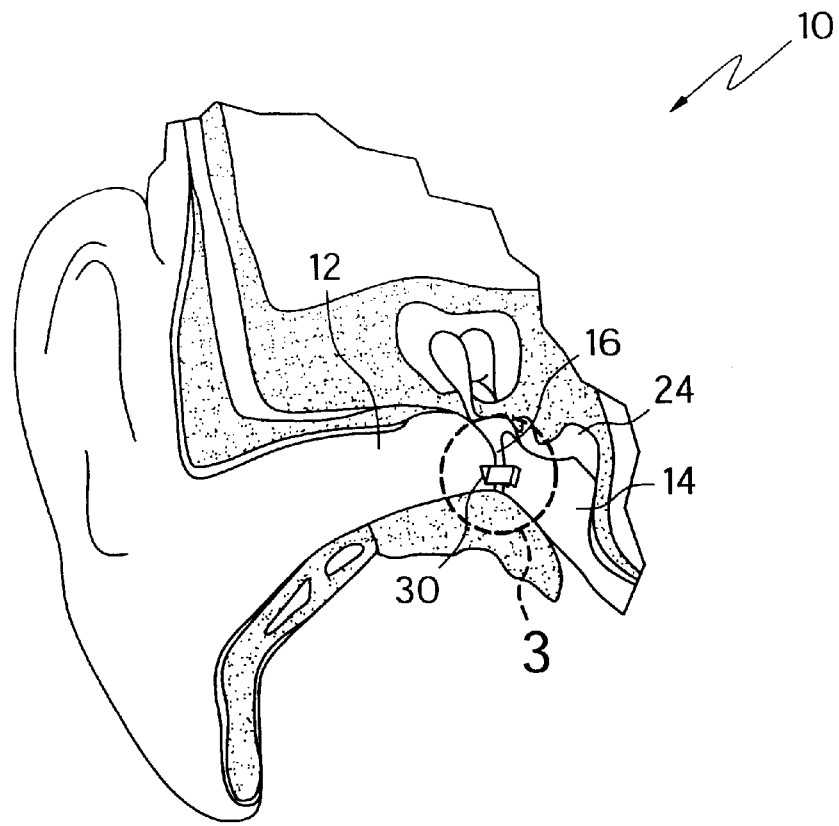
FIG. 1 is a perspective view of an ear illustrating in particular a cross section of the middle and outer ear cavities separated by the tympanic membrane in which an ear vent device made in accordance with the present invention has been inserted.
Figure 2:
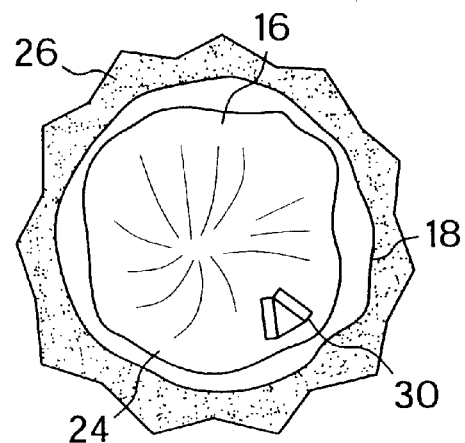
FIG. 2 is a schematic view of the tympanic membrane in which an ear vent device made in accordance with the present invention has been inserted.

Referring now to the drawing figures in detail, wherein like numerals indicate the same elements throughout the views, FIGS. 1 and 2 illustrate a typical ear which includes an outer or external ear cavity 12 and a middle ear cavity 14 separated by a tympanic membrane or ear drum 16. Vibrations caused by sound waves impinging of the tympanic membrane 16 are transmitted in the form of vibrations through a chain of three movable bones known as ossicles to the inner ear (not shown). The tympanic membrane 16 is generally cone shaped, with its concavity facing downwardly and outwardly toward the outer ear cavity 12. An outer ring 18, which connects the tympanic membrane 16 to surrounding bone 26, has fibrous tissue 24 radiating inwardly toward the membrane's center in a spoke-like fashion.

Figure 4:
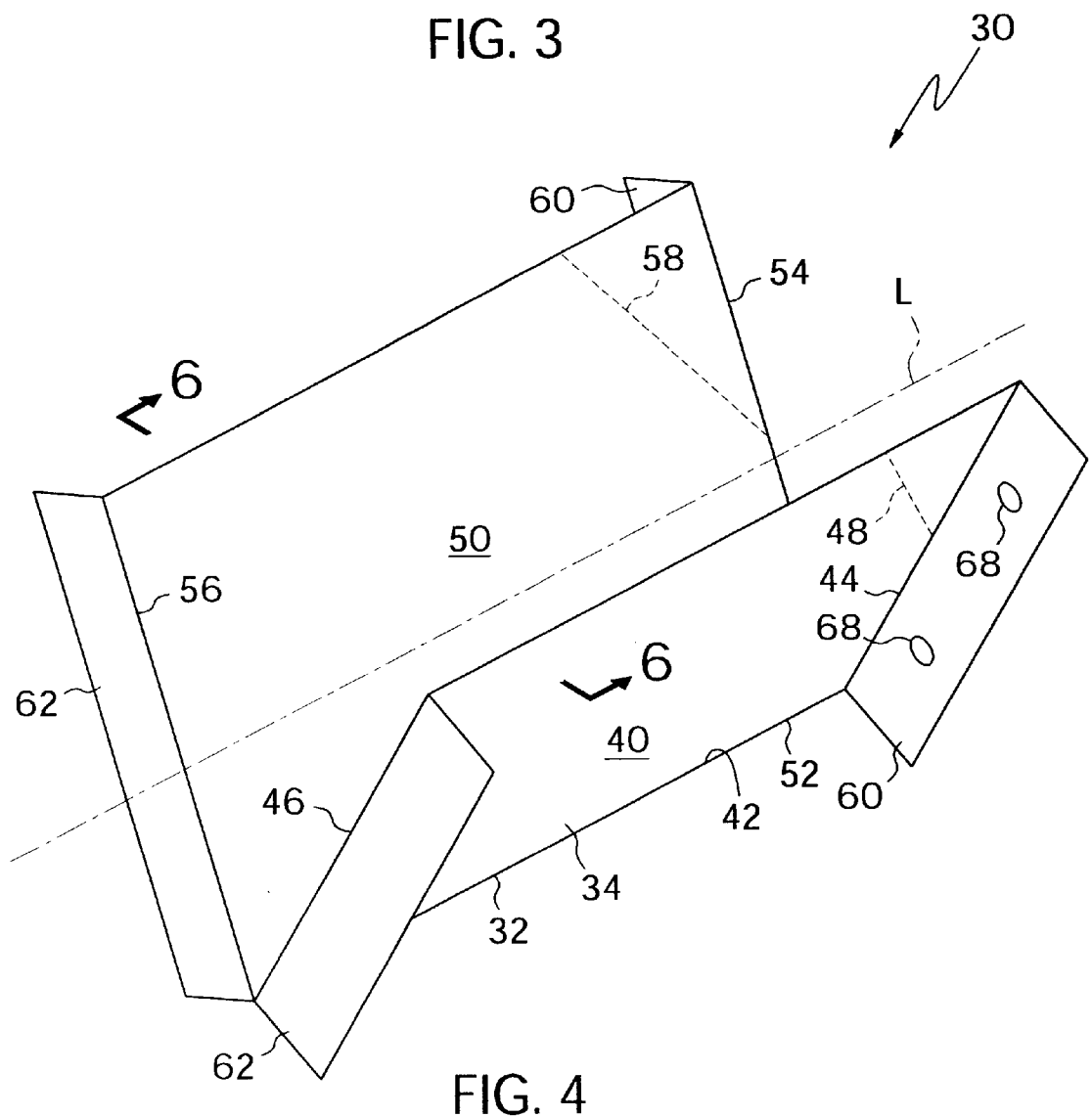
FIG. 4 is a perspective view of one embodiment of an ear vent device made in accordance with the present invention in an open operable condition.

Turning now to FIG. 4, the ear vent device 30 of the present invention is preferably configured in a generally V-shaped cross-section, or as a wedge shape. Device 30 has a longitudinal axis L, and can include a first panel 40 and a second panel 50, which can be preferably resiliently joined along or adjacent their respective longitudinal edges 42 and 52, respectively by an apex or hinge 32. Panels 40 and 50 should be sized and configured so as to maintain the passageway 28 provided in the tympanic membrane 16 in an open operable condition. While panel 40 and 50 are illustrated as being similarly sized and configured, the present invention contemplates that panels (e.g., 40) can have different sizes and be formed in different shapes from each other.

Panels 40 and 50 should each have a sufficient length so that the device 30 extends through the tympanic membrane 16 and effectively establishes and maintains fluid communication between the outer ear cavity 12 and middle ear cavity 14. Although the actual length will vary depending of the particular application, the longitudinal length of panels 40 and 50 can vary from about 2 mm to about 7 mm, and can be preferably about 4 mm.

Panels 40 and 50 are resiliently joined by apex 32 to maintain a conduit or channel therebetween, and to assist in retarding healing of the passageway or incision 28 in the tympanic membrane 16. Apex 32 is preferably either made of a softer resilient material, or less rigid, than panels 40 and 50 so that the device 30 can be easily folded up to a closed position (see FIG. 7) for insertion into and retraction from the tympanic membrane 16.

Figure 6:
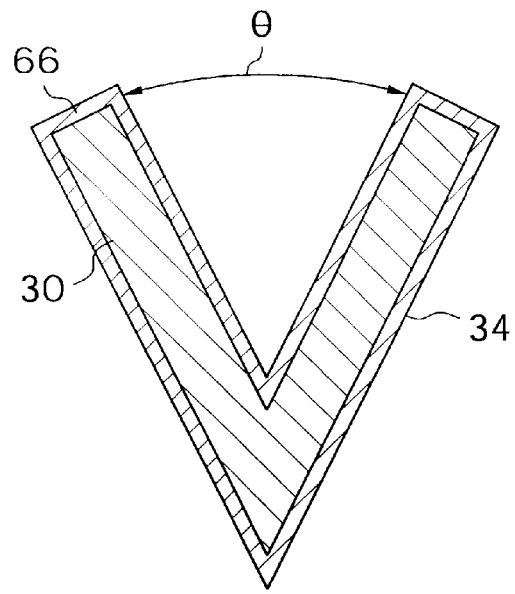
FIG. 6 is cross sectional view of an ear vent tube device taken along line 6—6 in FIG. 4 illustrating a coating over the ear vent device.

Turning now to FIG. 6, panels 40 and 50 are preferably provided to be angularly oriented to each other such that passageway 28 and device 30, when in an open operable condition, maintain sufficient fluid communication between the middle ear cavity 12 and the outer ear cavity 14. It is further preferable that device 30 have an open operable condition to assist in permitting the safe passage of devices and medication through the passageway 28. Suitable angular orientation Θ between panels 40 and 50 can vary from about 10 degrees to about 35 and can preferably be about 17 degrees.

Figure 3:
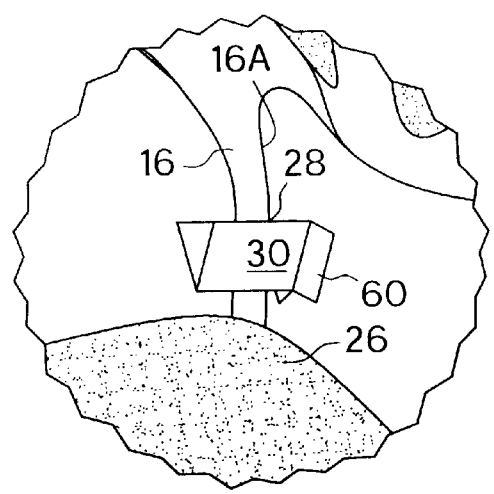
FIG. 3 is an enlarged sectional view of the ear in FIG. 1 further illustrating an ear vent device made in accordance with the present invention inserted into the tympanic membrane.

As illustrated in FIG. 4, a flange 60 can be provided adjacent at least one of the inner edges 44 and 54 of the panels 40 and 50, respectively, and preferably adjacent both of the inner edges 44 and 54. Flange 60 can serve to anchor the ear vent device 30 to the tympanic membrane 16 so as to inhibit easy extrusion into the outer ear cavity 12. As illustrated, flange 60 are preferably oriented to rest against the inner surface 16A (see FIG. 3) of the tympanic membrane 16 and thus, extends generally perpendicular away from panels 40 and 50. Flange 60 is configured so that device 30 remains balanced when inserted in the tympanic membrane 16. While flanges 60 are illustrated in a rectangular shape, the present invention contemplates that flanges 60 can be configured in a variety of shapes and configurations, and also in a variety of sizes, depending on the desired application.

In an alternative embodiment of the present invention, a flange 62 can be provided adjacent either or both of the outer edges 46 and 56 of panels 40 and 50, respectively to assist in preventing the ear tube device 30 from falling into the middle ear cavity 14 while in situ.

Figure 5:
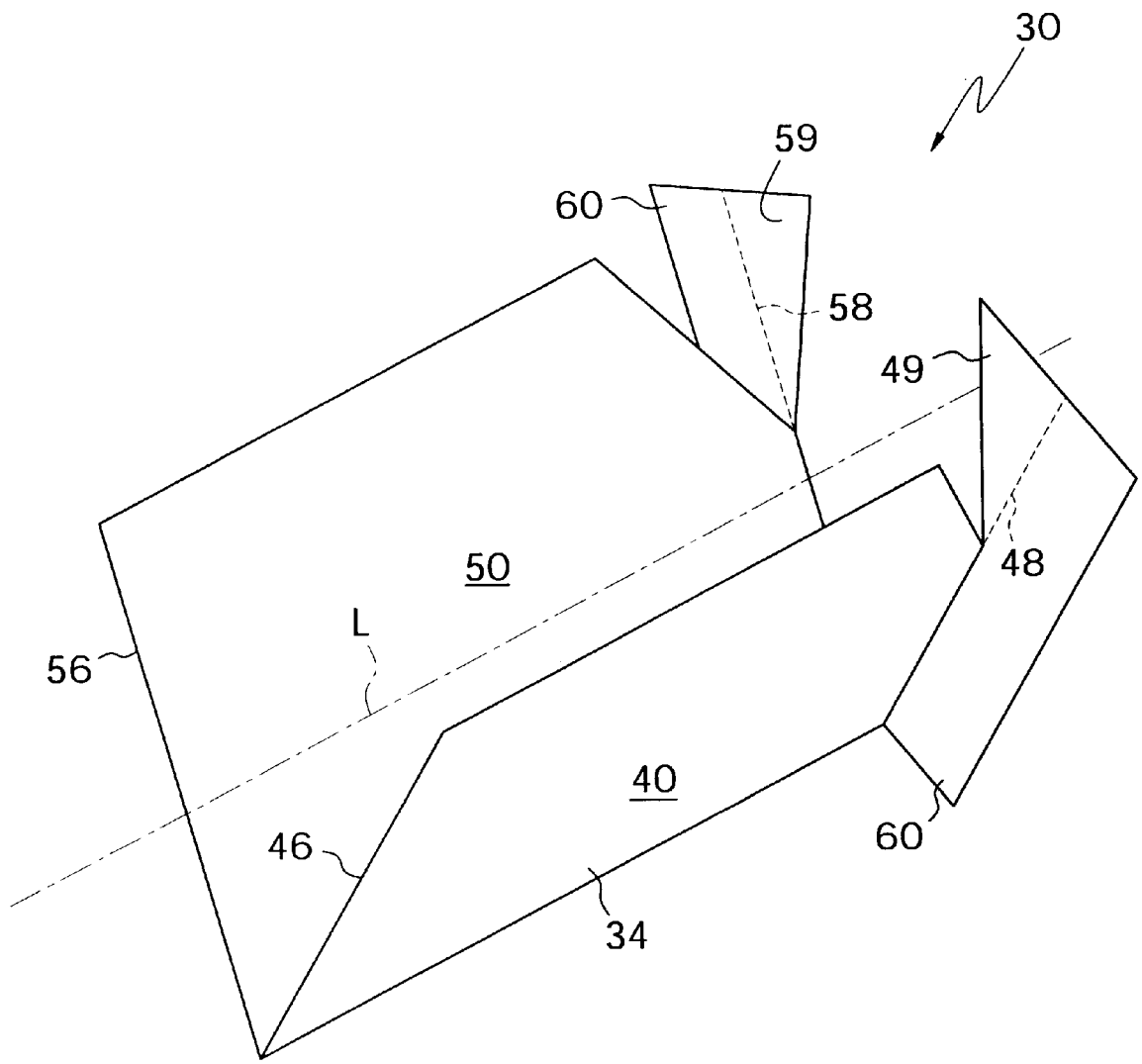
FIG. 5 is a perspective view of an alternative embodiment of an ear vent device made in accordance with the present invention in an open operable condition.

To increase the stability of the device 30 in the tympanic membrane 16, the surface area of the flange 60 can be increased by cutting panels 40 and/or 50 along cut lines 48 and 58, respectively, as illustrated by dashed lines in FIG. 5. Once the panels 40 and 50 have been cut, the enlarged flange portions 49 and 59, respectively, can be fold outwardly toward flanges 60, respectively, so as to further assist in inhibiting device 30 from being extruded from the tympanic membrane 16.

Openings or holes 68 can be provided on flanges 60 or 62 to provide an enhanced site for forceps or other surgical instruments to grasp the device 30 so as to ease or facilitate insertion into or removal from the tympanic membrane 16. Moreover, such openings 68 can also assist tissue 20 ingrowth on flange 60 so as to assist in securing or stabilizing the device 30 in the tympanic membrane 16.

Panels 40 and 50 and flanges 60 and/or 62 preferably are formed as a unitary piece using techniques and equipment standard in the industry. More specifically, device 30 can be molded in generally the desired open operable condition, or can be folded and/or scored so that panels 40 and 50, and flanges 60 and 62 resiliently bend or fold accordingly to accomplish the objectives of the present invention.

A variety of standard biocompatable materials available in the industry can be used to form the device 30. The material should have sufficient wear properties so that it is sufficiently pliable for movement between the open and closed positions so that it is sufficiently rigid and maintains its structural integrity in the desired form and orientation in situ. More specifically, for insertion into the tympanic membrane 16, panels 40 and 50, apex 32, and flanges 60 and 62 should be made of a material so that they can be folded together in a closed position (see FIG. 7) whereby the panels 40 and 50 are essentially parallel to each other and the flanges 60 and 62 are parallel to the panels 40 and 50.

After insertion, the material of device 30 should be such that the device 30 resiliently returns to and maintains the device in the open operable condition, as detailed above and illustrated in FIGS. 4 and 5. Flanges 60 and 62 should be either resilient or flexible so that they unfold and remain in an extended position whereby they extend generally perpendicular away from panels 40 and 50. Illustrative examples of materials which might be used include plastics, such as a polyethylene resin; or rubber, such as a medical grade silicone.

When long term use is contemplated or desired, the material for device 30 can be formed with a porous outer surface or one which encourages surface adhesion of surrounding tissue 20, preferably limited tissue ingrowth, to the device 30. The pores should be large enough so that some tissue ingrowth in the form of collagen fibers will occur, especially on panels 40 and 50. In some instances, however, the pores should be small enough so that trauma to the tympanic membrane 16 can be minimized when the device 30 is removed. Examples of suitable materials may include porous ultra-high molecular weight polyethylene, dense hydroxylapatite, titanium with a matte surface formed by chemical etching.

Turning now to FIG. 6, it is further contemplated that the device 30 might be coated, in part or in whole, with a coating 66. Coating 66 can be applied to the panels 40 and 50, flanges 60 and 62, and apex 32 using a variety of standard techniques and methods known in the industry, such as spraying or dipping. Coating 66 can be one of a variety of standard biocompatible materials that assists in preventing the clogging of the conduit provided between the panels 40 and 50, and apex 32. Moreover, when short term usage of the device 30 is contemplated, coating 66 can be one of a variety of standard biocompatible materials that assists in preventing or inhibiting the tissue 20 of the tympanic membrane 16 from adhering to or integrating with the device 30. Illustrative examples of materials which might be used include a copolymer of methacrylate acid glycol, mannitol, fluorine-containing resins, or a combination of these materials.

Alternatively, in contemplated longer term usage, the coating 66 may be one of a variety of standard biocompatible materials that assists in enhancing adherence of tissue 20 to the device 30 so as to further stabilize the device 30 and assist in preventing extruding of the device 30. Coating 66 could also include one of a variety of standard anti-coagulating, anti-bacterial or anti-fungal compositions, as desired.

It is alternatively contemplated that the materials of coating 66 may be embedded or formed in the material of the device 30, and preferably adjacent its outer surface 34.

Figure 7:
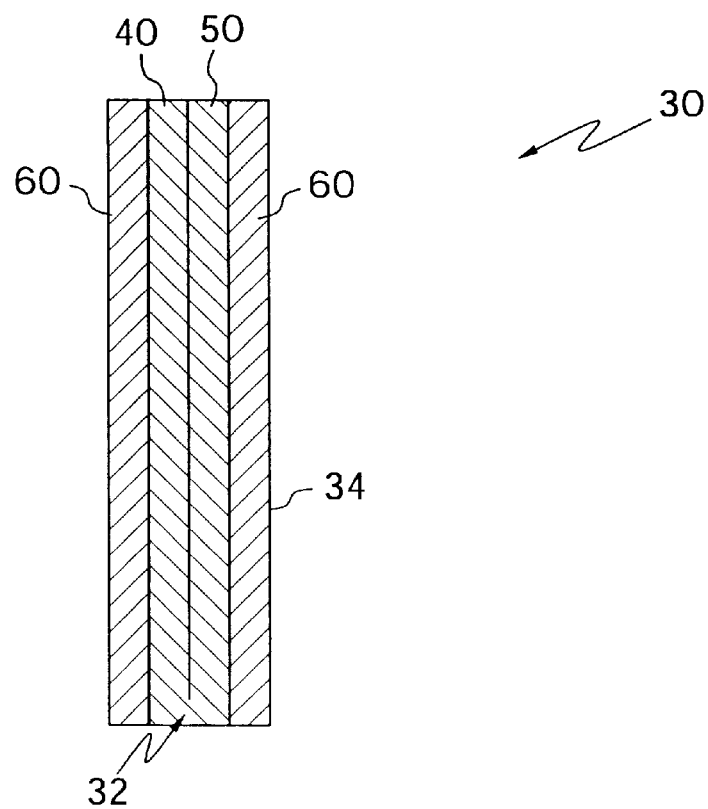
FIG. 7 is a cross sectional view of an ear vent device made in accordance with the present invention in a closed condition.

In use, as illustrated in FIGS. 1, 2, 3 and 6, device 30 is implanted into the tympanic membrane 16 to maintain passageway 28 in an open condition. The procedure for inserting the device includes providing a small passageway or incision 28, preferably a linear cut, in the tissue 20 that extends generally parallel to fibers 22 using techniques and instruments known in the industry. Next, panels 40 and 50, and flanges 60 and 62 are manipulated to be placed in the collapsed or closed position, as illustrated in FIG. 7, so as to reduce the width of device 30. The device 30 is then grasped by forceps or other devices known and used in the industry for placement of tubes in the tympanic membrane 16, and inserted into the passageway 28.

The flanges 60 and 62 are unfolded, either due to their resilient nature, with assistance, or due to both, to the extended position, as illustrated in FIGS. 4–5 to assist in inhibiting the device 30 from being extruded from the tympanic membrane 16 into the outer ear cavity 12. The panels 40 and 50 likewise are unfolded, either due to their resilient nature, with assistance, or due to both, to the open operable position, as illustrated in FIGS. 4–5. Fluid communication is thus established and maintained between the outer ear cavity 12 and the middle ear cavity 14.

Turning back to FIG. 4, the resistance to extrusion of the device 30 can be further inhibited by cutting the panels 40 and 50 along cut lines 48 and 58, respectively. The enlarged flange portions 49 and 59 can then be moved or folded to be oriented substantially parallel to the flange 60.

To remove the device 30 from the tympanic membrane 16, a surgical device is inserted into the ear 10 and the device 30 is collapsed such the it can be slid out of the passageway 28 while minimizing trauma to the tympanic membrane 16.

Having shown and described the preferred embodiments of the present invention in detail, it will be apparent that modifications and variations by one of ordinary skill in the art are possible without departing from the scope of the present invention defined in the appended claims. Several potential modifications have been mentioned and others will be apparent to those skilled in the art. Accordingly, the scope of the present invention should be considered in terms of the following claims and is understood not to be limited to the details of structure and operation shown and described in the specification and drawings.

I claim:

1. An eardrum vent device, said device having a longitudinal axis and comprising:
   a first panel having a first edge, and
   a second panel resiliently joined to said first panel along an apex in a substantially open, angular arrangement, said apex extending substantially parallel to said longitudinal axis,
   wherein said device being sized and configured to maintain an aperture in ear tissue in an operable open condition.

2. The device of claim 1, wherein said device further comprising a flange attached adjacent said first edge.

3. The device of claim 2, wherein said second panel comprises a first edge and a flange adjacent said first edge of said second panel.

4. The device of claim 2, wherein said flange being oriented relative to said first panel at an angle about 90 degrees.

5. The device of claim 2, wherein said flange comprises at least one opening.

6. The device of claim 1, wherein said first panel and said second panel being angularly oriented to each other at an angle from about 10 degrees to about 35 degrees.

7. The device of claim 6, wherein said angle is about 17 degrees.

8. The device of claim 1, wherein said device is made from a pliable material.

9. The device of claim 1, wherein said device is made from plastic.

10. The device of claim 1, wherein at least a portion of said device is provided with an outer coating.

11. The device of claim 1, wherein said first panel comprising a portion that is foldable to be oriented parallel to the second panel.

12. The device of claim 1, wherein said device has an outer surface comprising a material to encourage tissue adherence.

13. The device of claim 1, wherein said device has an outer surface comprising a material to inhibit tissue adherence.

14. A method for maintaining an aperture in a lining of an ear, comprising the steps of:
   providing an eardrum vent tube having a longitudinal axis that comprises a first panel having a first edge;
   a second panel resiliently joined to said first panel along an apex in a substantially open, angular arrangement, said apex extending substantially parallel to said longitudinal axis;
   making an incision in the lining of the ear; and
   inserting said device in said incision.

15. The method of claim 14, further comprising the step of:
   collapsing the device to a closed position prior to inserting said device.

16. The method of claim 14, further comprising the step of:
   unfolding said device to an open operable condition.

17. The method of claim 14, further comprising the step of: removing said device from said ear.

18. The method of claim 17 further comprising the step of collapsing said device from an operable open condition to a closed position.

19. An eardrum vent device, said device comprising:
   a first panel having a first edge, a second edge oppositely disposed from said first edge, and a flange attached adjacent each said first and second edges; and
   a second panel resiliently joined to said first panel along an apex in a substantially open, angular arrangement, said second panel comprising a first edge and a second edge oppositely disposed from said first edge, and a flange being attached adjacent each of said first and second edges of said second panel,
   wherein said device being sized and configured to maintain an aperture in ear tissue in an operable open condition.

20. A method for maintaining an aperture in a lining of an ear, said method comprising the steps:
   providing an eardrum vent device that comprises a first panel having a first edge, a second panel having a first edge and resiliently joined to said first panel along an apex in a substantially open, angular arrangement, and a flange substantially parallel to said first and second panels;
   cutting a portion of one of said panels near said first edge;
   folding said cut portion of said panel to be substantially parallel to said flange;
   making an incision of the lining of the ear; and
   inserting said device in said incision.

* * * * *

UNITED STATES PATENT AND TRADEMARK OFFICE
CERTIFICATE OF CORRECTION

PATENT NO. : 6,027,532
DATED : February 22, 2000
INVENTOR(S) : Claude P. Hobeika It is certified that error appears in the above-identified patent and that said Letters Patent is hereby corrected as shown below:

In Claim 14, column 8, line 12, replace "tube" with --device--.

Signed and Sealed this

Twentieth Day of February, 2001

Attest:

NICHOLAS P. GODICI

*Attesting Officer*  *Acting Director of the United States Patent and Trademark Office*